(12) United States Patent
Bischoff et al.

(10) Patent No.: US 7,630,873 B2
(45) Date of Patent: Dec. 8, 2009

(54) APPROXIMATING EIGENSOLUTIONS FOR USE IN DETERMINING THE PROFILE OF A STRUCTURE FORMED ON A SEMICONDUCTOR WAFER

(75) Inventors: Joerg Bischoff, Ilmenau (DE); Karl Hehl, Jena (DE); Xinhui Niu, Los Altos, CA (US); Wen Jin, Sunnyvale, CA (US)

(73) Assignee: Tokyo Electron Limited, Tokyo (JP)

( * ) Notice: Subject to any disclaimer, the term of this patent is extended or adjusted under 35 U.S.C. 154(b) by 1606 days.

(21) Appl. No.: 10/375,708

(22) Filed: Feb. 26, 2003

(65) Prior Publication Data

US 2004/0167754 A1 Aug. 26, 2004

(51) Int. Cl.
*G06F 17/50* (2006.01)
(52) U.S. Cl. ........................................ 703/13
(58) Field of Classification Search .................... 703/13
See application file for complete search history.

(56) References Cited

U.S. PATENT DOCUMENTS

| | | | | |
|---|---|---|---|---|
| 5,896,300 | A * | 4/1999 | Raghavan et al. | 716/10 |
| 6,219,142 | B1 * | 4/2001 | Kane | 356/450 |
| 2001/0051856 | A1 * | 12/2001 | Niu et al. | 702/57 |
| 2004/0078173 | A1 * | 4/2004 | Bischoff et al. | 703/2 |
| 2005/0068545 | A1 * | 3/2005 | Niu et al. | 356/625 |

FOREIGN PATENT DOCUMENTS

| | | |
|---|---|---|
| WO | WO 01/55669 A1 | 8/2001 |
| WO | WO 2004/036142 A2 | 4/2004 |

OTHER PUBLICATIONS

Schultz, Stephen, VOL_RCWA computes the diffraction efficiencies of a planar volume grating by the Rigorous Coupled Wave Analysis, www.ee.byu.edu/class/ee662fall2004sec1/homework/vol_rcwa.m, 2002.*
Song Peng and G. Michael Morris, Efficient and stable implementation of rigorous coupled-wave analysis for surface-relief gratings, The Institute of Optics, University of Rochester, Proceedings of SPIE—vol. 2532. 1995.*
S. Peng and G. M. Morris, Efficient implementation of rigorous coupled-wave analysis for surface-relief gratings, 1995, vol. 12, No. 5/May 1995/J. Opt. Soc. Am. A, pp. 1087-1096.*

(Continued)

*Primary Examiner*—Kamini S Shah
*Assistant Examiner*—David Silver
(74) *Attorney, Agent, or Firm*—Manuel B. Madriaga

(57) ABSTRACT

Eigensolutions for use in determining the profile of a structure formed on a semiconductor wafer can be approximated by obtaining a known set of eigenvectors associated with a first section of a hypothetical profile of the structure, where the known set of eigenvectors is used to generate a simulated diffraction signal for the hypothetical profile. A known characteristic matrix associated with a second section of a hypothetical profile is obtained, and an approximated set of eigenvalues for the second section is determined based on the known set of eigenvectors associated with the first section and the known characteristic matrix associated with the second section.

39 Claims, 5 Drawing Sheets

OTHER PUBLICATIONS

Philippe Lalanne and Eric Silberstein, Fourier-modal methods applied to waveguide computational problems, Optics Letters / vol. 25, No. 15 / Aug. 1, 2000, pp. 1092-1094.*

Xinhui Niu et al, Specular Spectroscopic Scatterometry, IEEE Transactions on Semiconductor Manufacturing, vol. 14, No. 2, May 2001, pp. 97-111.*

Xinhui Niu, An Integrated System of Optical Metrology for Deep Sub-Micron Lithography, berkeley, May 6, 1999.*

Xinhui Niu et al, Specular Spectroscopic Scatterometry in DUV Lithography, Microlithography, SPIE '99, 159-168.*

UK Search Report mailed on Jul. 15, 2004, for UK patent application No. GB 0403040.9 filed on Feb. 11, 2004, 2 pages.

* cited by examiner

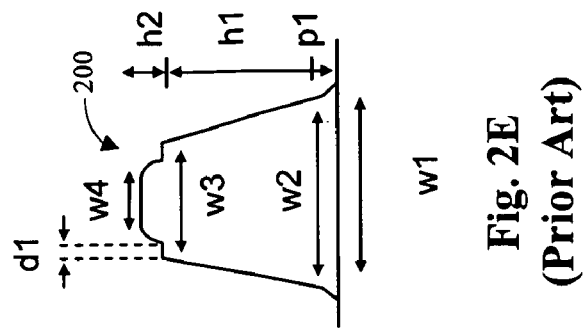
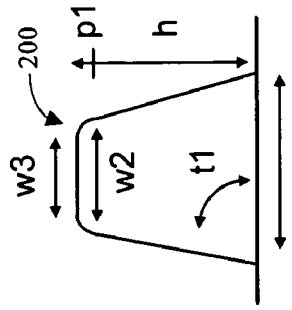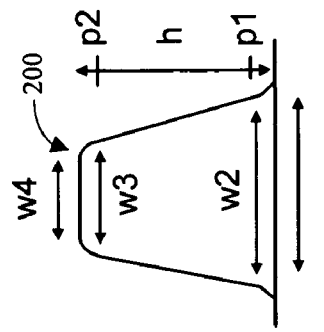
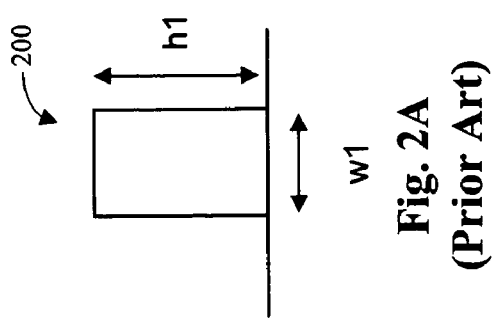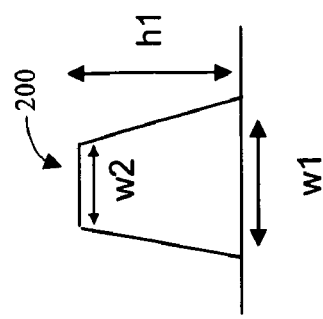

APPROXIMATING EIGENSOLUTIONS FOR USE IN DETERMINING THE PROFILE OF A STRUCTURE FORMED ON A SEMICONDUCTOR WAFER

BACKGROUND

1. Field of the Invention

The present application relates to wafer metrology, and more particularly to approximating eigensolutions for use in determining the profile of a structure formed on a semiconductor wafer.

2. Related Art

Optical metrology can be utilized to determine the profile of structures formed on semiconductor wafers. In general optical metrology involves directing an incident beam at a structure and measuring the resulting diffraction beam. The characteristics of the measured diffraction beam (i.e., a measured diffraction signal) is typically compared to pre-determined diffraction signals (i.e., simulated diffraction signals) that are associated with known profiles. When a match is made between the measured diffraction signal and one of the simulated diffraction signals, then the profile associated with the matching simulated diffraction signal is presumed to represent the profile of the structure.

In general, the process of generating a simulated diffraction signal involves performing a large number of complex calculations, which can be time and computationally intensive. The number and complexity of the calculations increases for structures having profiles that vary in more than one dimension.

SUMMARY

In one exemplary embodiment, eigensolutions for use in determining the profile of a structure formed on a semiconductor wafer can be approximated by obtaining a known set of eigenvectors associated with a first section of a hypothetical profile of the structure, where the known set of eigenvectors is used to generate a simulated diffraction signal for the hypothetical profile. A known characteristic matrix associated with a second section of a hypothetical profile is obtained, and an approximated set of eigenvalues for the second section is determined based on the known set of eigenvectors associated with the first section and the known characteristic matrix associated with the second section.

DESCRIPTION OF DRAWING FIGURES

The present invention can be best understood by reference to the following description taken in conjunction with the accompanying drawing figures, in which like parts may be referred to by like numerals:

FIGS. 2A-2E depict various hypothetical profiles of a structure;

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
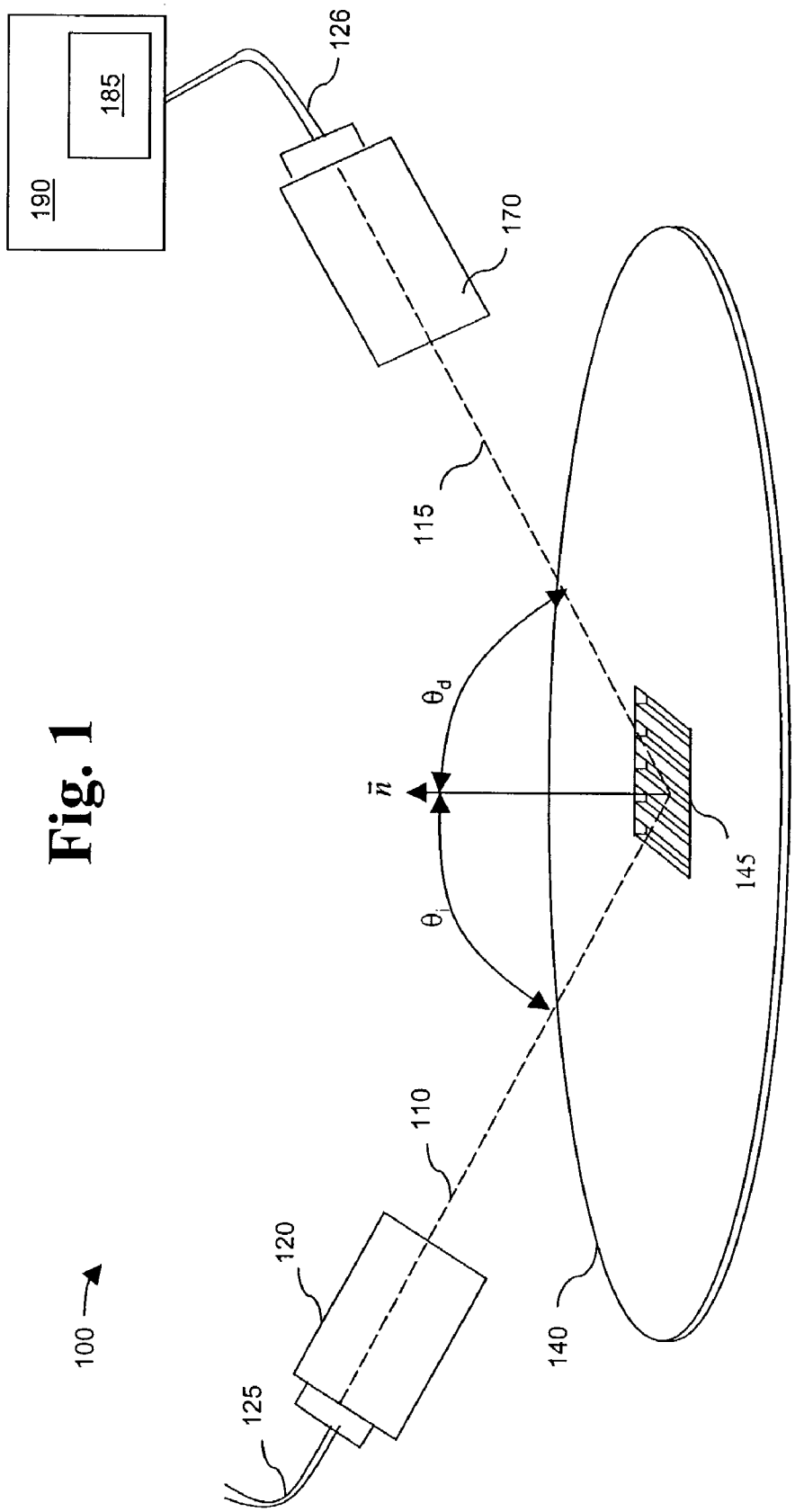
FIG. 1 depicts an exemplary optical-metrology system.

In one exemplary embodiment, optical-metrology can be utilized to determine the profile of a structure formed on a semiconductor wafer. As depicted in FIG. 1, an optical-metrology system 100 can include an electromagnetic source 120, such as an ellipsometer, reflectometer, and the like. A structure 145 is illuminated by an incident beam 110 from electromagnetic source 120. Incident beam 110 is directed onto structure 145 at an angle of incidence $\theta_i$ with respect to normal $\vec{n}$ of structure 145. Diffraction beam 115 leaves at an angle of $\theta_d$ with respect to normal $\vec{n}$.

As depicted in FIG. 1, diffraction beam 115 is received by detector 170. When electromagnetic source 120 is an ellipsometer, the relative magnitude ($\Psi$) and the phase ($\Delta$) of diffraction beam 115 are received and detected. When electromagnetic source 120 is a reflectometer, the relative intensity of diffraction beam 115 is received and detected.

To determine the profile of structure 145, optical-metrology system 100 includes a processing module 190, which converts diffraction beam 115 received by detector 170 into a diffraction signal (i.e., a measured diffraction signal). As described below, the profile of structure 145 can then be determined using either a library-based process or a regression-based process.

2. Library-Based Process of Determining Profile of Structure

In a library-based process of determining the profile of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 190 compares the measured diffraction signal to simulated diffraction signals stored in a library 185. Library 185 includes simulated diffraction signals that are associated with hypothetical profiles of structure 145. More particularly, in one exemplary embodiment, library 185 includes pairings of simulated diffraction signals and hypothetical profiles of structure 145. The simulated diffraction signal in each pairing includes hypothetically generated reflectances that characterize the predicted behavior of diffraction beam 115 assuming that the profile of the structure 145 is that of the hypothetical profile in the simulated diffraction signal and hypothetical profile pairing.

The set of hypothetical profiles stored in library 185 can be generated by characterizing a hypothetical profile using a set of parameters, then varying the set of parameters to generate hypothetical profiles of varying shapes and dimensions. The process of characterizing a profile using a set of parameters can be referred to as parameterizing.

For example, as depicted in FIG. 2A, assume that hypothetical profile 200 can be characterized by parameters h1 and w1 that define its height and width, respectively. As depicted in FIGS. 2B to 2E, additional shapes and features of hypothetical profile 200 can be characterized by increasing the number of parameters. For example, as depicted in FIG. 2B, hypothetical profile 200 can be characterized by parameters h1, w1, and w2 that define its height, bottom width, and top width, respectively. Note that the width of hypothetical profile 200 can be referred to as the critical dimension (CD). For example, in FIG. 2B, parameter w1 and w2 can be described as defining the bottom CD and top CD, respectively, of hypothetical profile 200.

As described above, the set of hypothetical profiles stored in library 185 (FIG. 1) can be generated by varying the parameters that characterize the hypothetical profile. For example, with reference to FIG. 2B, by varying parameters h1, w1, and w2, hypothetical profiles of varying shapes and dimensions can be generated. Note that one, two, or all three parameters can be varied relative to one another.

With reference again to FIG. 1, the number of hypothetical profiles and corresponding simulated diffraction signals in the set of hypothetical profiles and simulated diffraction signals stored in library 185 (i.e., the resolution and/or range of library 185) depends, in part, on the range over which the set of parameters and the increment at which the set of parameters are varied. In one exemplary embodiment, the hypothetical profiles and the simulated diffraction signals stored in library 185 are generated prior to obtaining a measured diffraction signal from an actual structure. Thus, the range and increment (i.e., the range and resolution) used in generating library 185 can be selected based on familiarity with the fabrication process for a structure and what the range of variance is likely to be. The range and/or resolution of library 185 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-Based Process of Determining Profile of Structure

In a regression-based process of determining the profile of a structure, the measured diffraction signal is compared to a simulated diffraction signal (i.e., a trial diffraction signal). The simulated diffraction signal is generated prior to the comparison using a set of parameters (i.e., trial parameters) for a hypothetical profile (i.e., a hypothetical profile). If the measured diffraction signal and the simulated diffraction signal do not match or when the difference of the measured diffraction signal and one of the simulated diffraction signals is not within a preset or matching criterion, another simulated diffraction signal is generated using another set of parameters for another hypothetical profile, then the measured-diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, processing module 190 can generate a simulated diffraction signal for a hypothetical profile, then compare the measured diffraction signal to the simulated diffraction signal. As described above, if the measured diffraction signal and the simulated diffraction signal do not match or when the difference of the measured diffraction signal an done of the simulated diffraction signals is within a preset or matching criterion, then processing module 190 can iteratively generate another simulated diffraction signal for another hypothetical profile. In one exemplary embodiment, the subsequently generated simulated diffraction signal can be generated using an optimization algorithm, such as global optimization techniques, which includes simulated annealing, and local optimization techniques, which includes steepest descent algorithm.

In one exemplary embodiment, the simulated diffraction signals and hypothetical profiles can be stored in a library 185 (i.e., a dynamic library). The simulated diffraction signals and hypothetical profiles stored in library 185 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. As will be described below, in one exemplary embodiment, simulated diffraction signals can be generated by applying Maxwell's equations and using a numerical analysis technique to solve Maxwell's equations. More particularly, in the exemplary embodiment described below, rigorous coupled-wave analysis (RCWA) is used. It should be noted, however, that various numerical analysis techniques, including variations of RCWA, can be used.

In general, RCWA involves dividing a profile into a number of sections, slices, or slabs (hereafter simply referred to as sections). For each section of the profile, a system of coupled differential equations generated using a Fourier expansion of Maxwell's equations (i.e., the components of the electromagnetic field and permittivity ($\in$)). The system of differential equations is then solved using a diagonalization procedure that involves eigenvalue and eigenvector decomposition (i.e., eigen-decomposition) of the characteristic matrix of the related differential equation system. Finally, the solutions for each section of the profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

Figure 4:
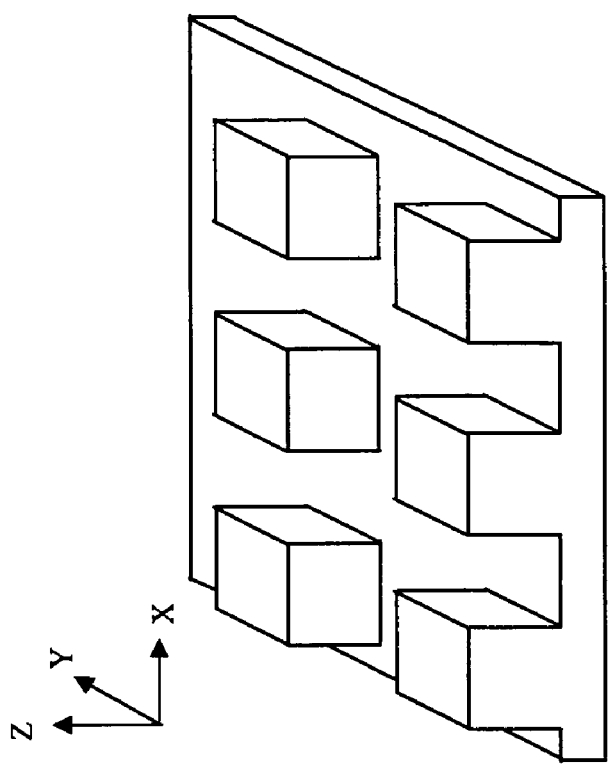
FIG. 4 depicts an exemplary two-dimension structure.
Figure 3:
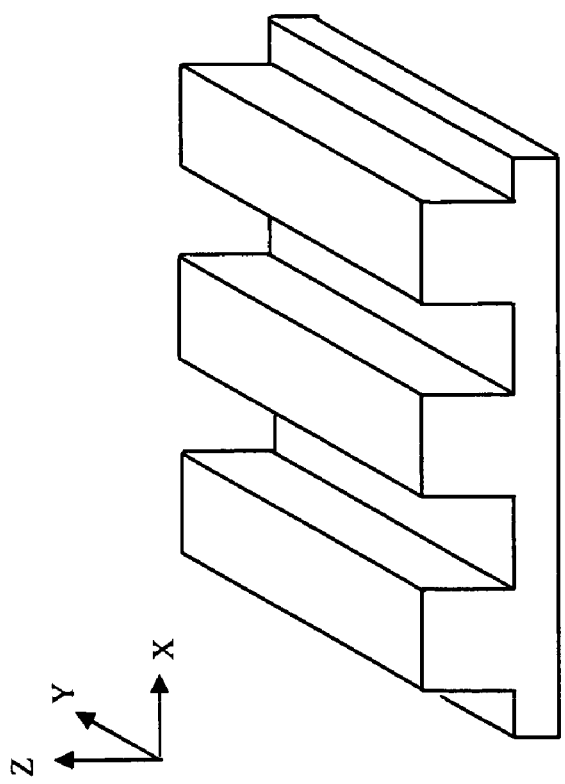
FIG. 3 depicts an exemplary one-dimension structure.

With reference to FIG. 3, RCWA can be used to determine the profile of a structure with a profile that varies in one dimension (i.e., the x-direction), which is assumed to be substantially uniform or continuous in the y-direction. With reference to FIG. 4, RCWA can be used to determine the profile of a structure with a profile that varies in at two dimensions (i.e., the x-direction and the y-direction). For the sake of example, a checkerboard grating is depicted in FIG. 4 as a structure having a profile that varies in two-dimensions. It should be recognized, however, that various types of structures can have profiles that vary in two or more dimensions, such as contact holes, posts, and the like. For a more detailed description of using RCWA with a structure having a profile that various in two or more dimensions, see U.S. patent application Ser. No. 10/274,252, titled GENERATING SIMULATED DIFFRACTION SIGNALS FOR TWO-DIMENSIONAL STRUCTURES, filed on Oct. 17, 2002, which is incorporated herein by reference in its entirety.

5. Approximating Eigensolutions

As described above, the process of generating a simulated diffraction signal can involve performing a large number of complex calculations. Additionally, as the complexity of the hypothetical profile increases, so does the number and complexity of the calculations needed to generate the simulated diffraction signal for the hypothetical profile.

More specifically, as also described above, when RCWA is used to generate simulated diffraction signals, a hypothetical profile is divided into a number of sections. For each section, a system of coupled differential equations are solved using a diagonalization procedure that involves eigenvalue and eigenvector decomposition of the characteristic matrix of the related differential equation system (i.e., eigensolution).

In one exemplary embodiment, rather than solving a system of coupled differential equations for every section, a set of eigenvalues associated with one section of a hypothetical profile is derived from a known set of eigenvectors associated with another section of a hypothetical profile. A set of eigenvectors associated with one section of a hypothetical profile is also derived from the known set of eigenvectors associated with another section of a hypothetical profile.

For example, assume that a system of coupled differential equations were solved for a first section of a hypothetical profile. Thus, a set of eigenvalues, a set of eigenvectors, and a characteristic matrix associated with the first section of the hypothetical profile are known. Now assume that a set of eigenvalues is to be determined for a second section of a hypothetical profile. In the present exemplary embodiment, rather than solving another system of coupled differential equations for the second section, a set of eigenvalues can be derived from the known set of eigenvectors associated with the first section.

Figure 5:
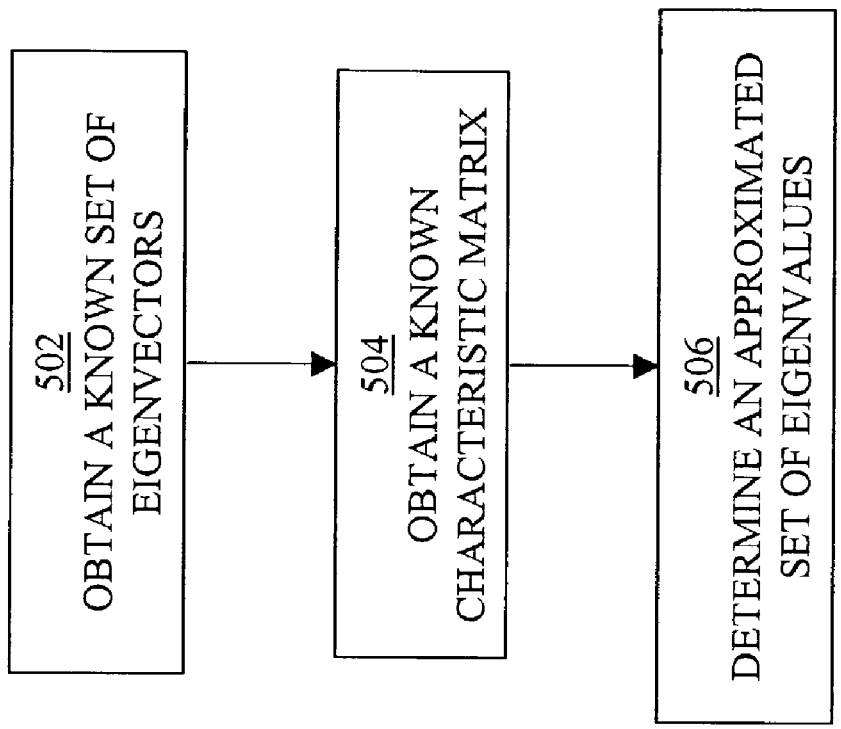
FIG. 5 is an exemplary process to determine an approximated set of eigenvalues.

More specifically, with reference to FIG. 5, in the present exemplary embodiment, in step 502, a known set of eigenvectors associated with the first section of a hypothetical profile is obtained. In step 504, a known characteristic matrix for the second section of a hypothetical profile is obtained. The characteristic matrix for the second section can be derived using RCWA from incident light properties and the geometry of the second section. In step 506, an approximated set of eigenvalues is determined based on the known set of eigenvectors associated with the first section and the known characteristic matrix for the second section.

In one exemplary embodiment, a set of eigenvalues for the second section is determined iteratively based on the known set of eigenvalues and the known set of eigenvectors associated with the first section. Again, assume that a system of coupled differential equations were solved for the first section. Thus, a set of eigenvalues, a set of eigenvectors, and a characteristic matrix associated with the first section are known.

Figure 6:
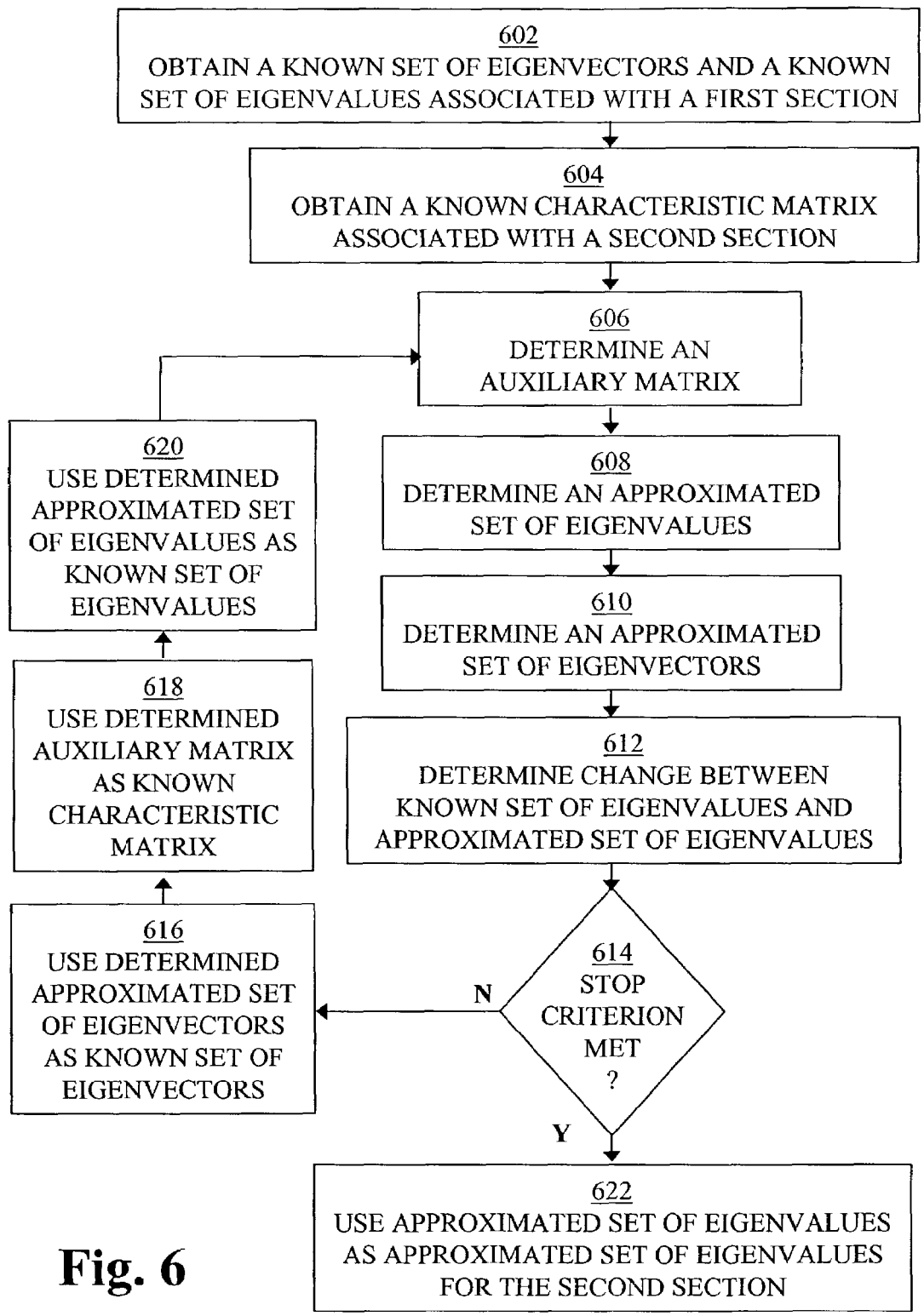
FIG. 6 is another exemplary process to determine an approximated set of eigenvalues.

With reference to FIG. 6, in step 602, a known set of eigenvectors and a known set of eigenvalues associated with the first section are obtained. In step 604, a known characteristic matrix associated with the second section is obtained. Again, the characteristic matrix for the second section can be derived using RCWA from incident light properties and geometry of the second section. In step 606, an auxiliary matrix is determined based on the known set of eigenvectors associated with the first section and the known characteristic matrix associated with the second section. In step 608, an approximated set of eigenvalues is determined based on the auxiliary matrix. In step 610, an approximated set of eigenvectors is determined based on the approximated set of eigenvalues and the auxiliary matrix.

In step 612, a change or difference between the known set of eigenvalues and the approximated set of eigenvalues is determined. In step 614, the determined change is compared to a stop criterion, such as a predetermined amount of change in the eigenvalues that is considered to be acceptable.

If the stop criterion is not met, steps 606 to 614 are repeated. When steps 606 to 614 are repeated, in step 616, the approximated set of eigenvectors determined in step 610 is used as the known set of eigenvectors in repeating step 606. Additionally, in step 618, the auxiliary matrix determined in step 606 is used as the known characteristic matrix in repeating step 606. Finally, in step 620, the approximated set of eigenvalues determined in step 608 is used as the known set of eigenvalues in repeating step 612.

If the stop criterion is met, in step 622, the approximated set of eigenvalues determined in step 608 is used as the approximated set of eigenvalues for the second section. Additionally, after the approximated set of eigenvalues for the second section is determined, a set of eigenvectors for the second section can be determined based on the known set of eigenvectors associated with the first section and one or more approximated sets of eigenvectors determined in step 610. Thus, if one iteration is needed to determine an approximated set of eigenvalues for the second section, a set of eigenvectors for the second section can be determined based on the known set of eigenvectors associated with the first section and the approximated set of eigenvectors determined in step 610. However, if two iterations are needed to determine an approximated set of eigenvalues for the second section, a set of eigenvectors for the second section can be determined based on the known set of eigenvectors associated with the first section, the approximated set of eigenvectors determined in the first iteration of step 610, and the approximated set of eigenvectors determined in the second iteration of step 610.

As described above, the first and second sections are portions of a hypothetical profile. It should be recognized that the first and second sections can be portions of the same hypothetical profile or portions of different hypothetical profiles. The first section can also correspond to a different material than the second section. For example, the first section can correspond to a dielectric material and the second section can correspond to a metal material.

As described above, a hypothetical profile can be characterized by one or more parameters. Thus, the first and second sections can be characterized by one or more parameters. It should be recognized that one or more parameters that characterize the first section can differ from one or more parameters that characterize the second section. For example, the first section can be characterized by a line width parameter or a pitch parameter that differs from the line width parameter or the pitch parameter that characterizes the second section.

As described above, the profile of a structure can vary in one dimension or in two or more dimensions. Thus, the first and second sections can correspond to profiles that vary in one dimension or in two or more dimensions.

In addition to differences in material, geometry (i.e., parameters that characterize the geometry of the sections), the first and second sections can be associated with various different characteristics. For example, in optical metrology using an incident light, the simulated diffraction signal generated for the first section can correspond to a different incident light wavelength than the simulated diffraction signal generated for the second section. The simulated diffraction signal generated for the first section can also correspond to a different angle of incidence for the incident light than the simulated diffraction signal generated for the second section. It should be recognized that the first and second sections can be associated with any combination of different characteristics.

In one exemplary embodiment, the diffraction signal generated for the second section is stored in a library of simulated diffraction signals used in a library-based process for determining the profile of a structure. Thus, in generating diffraction signals for the library, rather than solving a system of coupled differential equations for every section used in every hypothetical profile for the library, eigensolutions can be approximated for one section based on known eigensolutions of another section. In this manner, the amount of time needed to generate a library of simulated diffraction signals can be reduced.

In another exemplary embodiment, the diffraction signal generated for the second section is generated as part of a regression-based process for determining the profile of a structure. Thus, in generating diffraction signals for the regression-based process, rather than solving a system of coupled differential equations for every section used in every hypothetical profile, eigensolutions can be approximated for one section based on known eigensolutions of another section. In this manner, the amount of time needed to generate simulated diffraction signals in the regression-based process can be reduced.

6. Theory

The following description provides a more theoretical explanation for deriving eigensolutions for one section of a theoretical profile (i.e., the second section) based on know eigensolutions for another section of a theoretical profile (i.e., the first section).

More specifically, a diagonalization (d) for a characteristic matrix (D) can be found using a transformation matrix (W):

$$(d) = (W)(D)(W)^{-1} \quad (1)$$

Assume an eigensolution is given for a characteristic matrix $D^0$ for a similar problem:

$$(d^0) = (W^0)(D^0)(W^0)^{-1} \quad (2)$$

Now assume that the characteristic matrices differ only slightly. Then, the following transformation:

$$(D^1) = (W^0)(D)(W^0)^{-1} \equiv (d^0) + (\Delta D^1) \quad (3)$$

provides a nearly diagonal (auxiliary) matrix. By means of the following assumption:

$$(d) = (W^1)(D^1)(W^1)^{-1} \quad (4)$$

with the matrix $(W^1) = \exp((X)) \cong (1) + (X)$, a transformation with X is defined, which comprises only non-diagonal elements with $|X_{ij}| \ll 1$.

Employing the last two equations to determine (d), with the condition $(W)^{-1} \cong (1) - (X)$, the following equation can be obtained by neglecting quadratic terms in X:

$$(d) \cong ((1)+(X)))(D^1)((1)-(X)) \cong (D^1) - [(D^1),(X)]_- \quad (5)$$

Since $(D^1) \equiv (d^0) + (\Delta D^1)$ also contains perturbation terms, a first order approximation $(d^1)$ of the exact solution (d) is obtained by dropping all higher order terms:

$$(d) \cong (d^1) = (d)^0 + (\Delta D)^1 - [(d)^0,(X)]_- \quad (6)$$

Since the left hand side contains only diagonal elements, the non-diagonal elements on the right hand side should disappear likewise. The exchange operation $[d^0,X]$ does not contribute to the diagonal elements $(d^1)$ of the exact solution (d). Therefore, the following relation holds for the diagonal elements:

$$d_i \cong d^1_i = d^0_i = D^1_{ii}. \quad (7)$$

The disappearance of the non-diagonal elements on the left-hand-side provides the condition:

$$\Delta D^1_{i \neq j} - [d^0,X]_{i \neq j} = 0, \quad (8)$$

From this, a relation for the elements $X_{i \neq j}$ may be derived as follows:

$$X_{i \neq j} = \Delta D^1_{i \neq j}/(d^0_i - d^0_j) = D_{i,j}{}^1/(D_{i,i}{}^1 - D_{j,j}{}^1) \quad (9)$$

The above described process can be iterated starting from equation (2) by using the following transformation in place of equation (2):

$$D^2 = W^1 D^1 (W^1)^{-1} \equiv d^1 + \Delta D^2, \quad (10)$$

For the iteration, the exact value $W^1 = 1 + X + X^2/2! + \ldots$ and analogous the value of the inverse $(W^1)^{-1} = 1 - X + X^2/2! - $ (minus sign for odd exponent X-terms) ... has to be taken.

The iteration can continue until a stop criterion is met, such as:

$$Q = \Sigma_i |(d^{k+1}_i - d^k_i)/d^k_i|^2 \quad (11)$$

As can be seen from above, a degeneration of $(D^1)$ may be a problem since the expression is diverging in the case of two (nearly) identical eigenvalues at $\Delta D_{i,j} \neq 0$. However, potential degeneration of $(D^1)$ can be resolved using various known numerical techniques, which are also known as healing techniques.

For example, in order to force W to converge, the non-diagonal elements of X have to be less than $\in < 1$. If this is not the case, the matrix $D^1$ and the matrix $W^0$ have to be transformed appropriately. To this end, the corresponding four elements of $D^1$, namely $D_{i,i}$; $D_{j,j}$; $D_{i,j}$ and $D_{j,i}$ are extracted and put into a 2,2 sub-matrix $D_s$, which can be diagonalized by solving a quadratic equation. This leads to a 2,2 diagonal matrix $d_s$.

From this solution, a transformation matrix can be derived:

$$(\Gamma)(D) = (d)(\Gamma) \quad (12)$$

that is applied to the whole matrices W and $W^{-1}$, i.e., for W the rows with the indices i and j are changed correspondingly:

$$W'_{i,m} = \Gamma_{11} W_{i,m} + \Gamma_{12} W_{j,m}$$

$$W'_{j,m} = \Gamma_{21} W_{i,m} + \Gamma_{22} W_{j,m} \quad (13)$$

and for $W^{-1}$ the columns with the indices i and j have to be changed correspondingly:

$$W'_{m,i}{}^{-1} = W_{m,i}{}^{-1} \Gamma_{11}{}^{-1} + W_{m,j}{}^{-1} \Gamma_{21}{}^{-1}$$

$$W'_{m,j}{}^{-1} = W_{m,i}{}^{-1} \Gamma_{11}{}^{-1} + W_{m,j}{}^{-1} \Gamma_{21}{}^{-1} \quad (14)$$

where, m is a running index (from 1 thru n=matrix size).

Likewise, the matrix $D^1$ has to be transformed by means of:

$$D^{1'} = \Gamma \cdot D^1 \cdot \Gamma^{-1} \quad (15)$$

Unlike for W, here both columns and rows with the indices i and j are concerned.

These steps can be repeated iteratively while picking every time the biggest $X_{ij}$ element until all elements fulfill the criterion $< \in$.

After calculating $D^{1'}$, in accordance with equation (7), an approximated set of eigenvalues (i.e., d) can be generated based on W', $W^1$, and $D^{1'}$, calculated in accordance with equations (13), (14), and (15), respectively. A difference between the approximated set of eigenvalues and the known set of eigenvalues is determined.

If the difference does not meet a stop criterion, another approximated set of eigenvalues is determined using previously determined approximated set of eigenvalues as the known set of eigenvalues, the approximated set of eigenvectors calculated in accordance with equation (13) as the known set of eigenvectors, and the auxiliary matrix calculated in accordance with equation (15) as the known characteristic matrix. This process is repeated until the stop criterion is met or a maximum number of attempts is made.

If the difference meets a stop criterion, the approximated set of eigenvalues is used as the approximated set of eigenvalues for the second section. If the stop criterion was met during the first iteration, meaning that only one set of approximated set of eigenvalues and eigenvectors were calculated, then the approximated set of eigenvectors calculated in accordance with equation (13) is used as the approximated set of eigenvectors for the second section. However, if the stop criterion was met after two or more iterations, then the approximated set of eigenvectors for the second section is determined based on the approximated sets of eigenvectors calculated during the iterations. Thus, if two iterations are needed, the approximated set of eigenvectors for the second section is determined by multiplying the approximated set of eigenvectors calculated during the first iteration with the approximated set of eigenvectors calculated during the second iteration.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. Many other variations are also to be considered within the scope of the present invention.

We claim:

1. A method of approximating eigensolutions for use in determining a profile of a structure formed on a semiconductor wafer, the method comprising:
   obtaining a known set of eigenvectors associated with a first section of a hypothetical profile of the structure, wherein the known set of eigenvectors is used to generate a simulated diffraction signal for the hypothetical profile;
   obtaining a known characteristic matrix associated with a second section of a hypothetical profile; and
   determining an approximated set of eigenvalues for the second section based on the known set of eigenvectors associated with the first section and the known characteristic matrix associated with the second section.

2. The method of claim 1, wherein the first section and the second section are portions of the same hypothetical profile.

3. The method of claim 1, wherein the first section and the second section are portions of different hypothetical profiles.

4. The method of claim 1, wherein one or more parameters that characterize the first section is different than one or more parameters that characterize the second section.

5. The method of claim 4, wherein the one or more parameters that characterize the first section and the one or more parameters that characterize the second section includes a line width parameter.

6. The method of claim 4, wherein the one or more parameters that characterize the first section and the one or more parameters that characterize the second section includes a pitch parameter.

7. The method of claim 1, wherein the first section corresponds to a different material than the second section.

8. The method of claim 1, wherein the profile of the structure varies in a first dimension.

9. The method of claim 8, wherein the profile of the structure varies in at least a second dimension in addition to the first dimension.

10. The method of claim 1, further comprising:
   (a) obtaining a known set of eigenvalues associated with the first section;
   (b) determining an auxiliary matrix based on the known set of eigenvectors and the known characteristic matrix;
   (c) determining an approximated set of eigenvectors based on the auxiliary matrix;
   (d) determining the approximated set of eigenvalues based on the approximated set of eigenvectors and the auxiliary matrix; and
   (e) determining if a change between the known set of eigenvalues and the approximated set of eigenvalues meets a stop criterion;
     (i) when the stop criterion is not met, repeating steps (b) to (e) using the determined approximated set of eigenvectors as the known set of eigenvectors in repeating step (b) and the determined auxiliary matrix as the known characteristic matrix in repeating step (b) and the determined approximated set of eigenvalues as the known set of eigenvalues in repeating step (e), and
     (ii) when the stop criterion is met, using the approximated set of eigenvalues as the approximated set of eigenvalues for the second section.

11. The method of claim 10 further comprising:
   determining a set of eigenvectors for the second section based on the known set of eigenvectors associated with the first section and the one or more approximated sets of eigenvectors determined in step (c) of claim 10.

12. The method of claim 11, wherein the set of eigenvalues and the set of eigenvectors are used in solving a system of coupled differential equations in a rigorous coupled wave analysis to generate a simulated diffraction signal for the second section.

13. The method of claim 12, wherein the simulated diffraction signal generated for the first section corresponds to a first incident light wavelength and the simulated diffraction signal generated for the second section corresponds to a second incident light wavelength.

14. The method of claim 12, wherein the simulated diffraction signal generated for the first section corresponds to a first angle of incidence and the simulated diffraction signal generated for the second section corresponds to a second angle of incidence.

15. The method of claim 12, wherein the simulated diffraction signal for the second section is stored in a library for use in a library-based process for determining the profile of a structure.

16. The method of claim 15, wherein the library-based process comprises:
   obtaining a diffraction signal measured from directing an incident beam at the structure (a measured diffraction signal); and
   comparing the measured diffraction signal to one or more simulated diffraction signals stored in the library to determine the profile of the structure.

17. The method of claim 12, wherein the simulated diffraction signal is generated as part of a regression-based process for determining the profile of a structure.

18. The method of claim 17, wherein the regression-based process comprises:
obtaining a diffraction signal measured from directing an incident beam at the structure (a measured diffraction signal);
comparing the measured diffraction signal to a first simulated diffraction signal; and
when the difference of the measured diffraction signal and the first simulated diffraction signal is not within a matching criterion:
generating a second simulated diffraction signal; and
repeating the comparing step using the second simulated diffraction signal.

19. A method of approximating eigensolutions for use in determining a profile of a structure formed on a substrate, the method comprising:
(a) obtaining a known set of eigenvectors and a known set of eigenvalues associated with a first section of a hypothetical profile of the structure;
(b) obtaining a known characteristic matrix associated with a second section of a hypothetical profile of the structure;
(c) determining an auxiliary matrix based on the known set of eigenvectors and the known characteristic matrix;
(d) determining an approximated set of eigenvectors based on the auxiliary matrix;
(e) determining an approximated set of eigenvalues based on the approximated set of eigenvectors and the auxiliary matrix; and
(f) determining if a change between the known set of eigenvalues and the approximated set of eigenvalues meets a stop criterion;
(i) when the stop criterion is not met, repeating steps (c) to (f) using the determined approximated set of eigenvectors as the known set of eigenvectors in repeating step (c) and the determined auxiliary matrix as the known characteristic matrix in repeating step (c) and the determined approximated set of eigenvalues as the known set of eigenvalues in repeating step (f), and
(ii) when the stop criterion is met, using the approximated set of eigenvalues as an approximated set of eigenvalues for the second section.

20. The method of claim 19 further comprising:
determining a set of eigenvectors for the second section based on the known set of eigenvectors associated with the first section and the one or more approximated sets of eigenvectors determined in step (d).

21. The method of claim 20, wherein the set of eigenvalues and eigenvectors are used in solving a system of coupled differential equations in a rigorous coupled wave analysis to generate a simulated diffraction signal for the second section.

22. The method of claim 21, wherein the simulated diffraction signal calculated using the second section is stored in a library for use in a library-based process for determining the profile of a structure.

23. The method of claim 21, wherein the simulated diffraction signal for the second section is generated as part of a regression-based process for determining the profile of a structure.

24. A system to approximate eigensolutions for use in determining a profile of a structure formed on a semiconductor wafer, the system comprising:
a memory having:
a known set of eigenvectors associated with a first section of a hypothetical profile of the structure,
wherein the known set of eigenvectors is used to generate a simulated diffraction signal for the hypothetical profile, and
a known characteristic matrix associated with a second section of a hypothetical profile; and
a processor configured to determine an approximated set of eigenvalues for the second section based on the known set of eigenvectors associated with the first section and the known characteristic matrix associated with the second section.

25. The system of claim 24,
wherein the memory has a known set of eigenvalues associated with the first section; and
wherein the processor is configured to:
(a) determine an auxiliary matrix based on the known set of eigenvectors and the known characteristic matrix,
(b) determine an approximated set of eigenvectors based on the auxiliary matrix,
(c) determine an approximated set of eigenvalues based on the approximated set of eigenvectors and the auxiliary matrix, and
(d) determine if a change between the known set of eigenvalues and the approximated set of eigenvalues meets a stop criterion;
(i) when the stop criterion is not met, repeat (a) to (d) using the determined approximated set of eigenvectors as the known set of eigenvectors in repeating (a) and the determined auxiliary matrix as the known characteristic matrix in repeating (a) and the determined approximated set of eigenvalues as the known set of eigenvalues in repeating (d), and
(ii) when the stop criterion is met, use the approximated set of eigenvalues as the approximated set of eigenvalues for the second section.

26. The system of claim 25, wherein the processor is further configured to determine a set of eigenvectors for the second section based on the known set of eigenvectors associated with the first section and the one or more approximated sets of eigenvectors determined in (b) of claim 25.

27. The system of claim 26, wherein the set of eigenvalues and the set of eigenvectors are used in solving a system of coupled differential equations in a rigorous coupled wave analysis to generate a simulated diffraction signal for the second section.

28. The system of claim 27, wherein the simulated diffraction signal for the second section is stored in a library for use in a library-based system configured to determine the profile of a structure.

29. The system of claim 28, wherein the library-based system comprises:
a detector configured to measure a diffraction signal from an incident beam directed at the structure (a measured diffraction signal); and
a processor configured to compare the measured diffraction signal to one or more simulated diffraction signals stored in the library to determine the profile of the structure.

30. The system of claim 27, wherein the simulated diffraction signal for the second section is generated as part of a regression-based system configured to determine the profile of a structure.

31. The system of claim 30, wherein the regression-based system comprises:
a detector configured to measure a diffraction signal from an incident beam directed at the structure (a measured diffraction signal); and a processor configured to:
compare the measured diffraction signal to a first simulated diffraction signal, and
when the difference of the measured diffraction signal and the first simulated diffraction signal is not within a matching criterion:
generate a second simulated diffraction signal; and
comparing the measured diffraction signal to the second simulated diffraction signal.

32. A computer-readable storage medium containing computer executable instructions for causing a computer to approximate eigensolutions for use in determining a profile of a structure formed on a semiconductor wafer, comprising instructions for:
obtaining a known set of eigenvectors associated with a first section of a hypothetical profile of the structure,
wherein the known set of eigenvectors is used to generate a simulated diffraction signal for the hypothetical profile;
obtaining a known characteristic matrix associated with a second section of a hypothetical profile; and
determining an approximated set of eigenvalues for the second section based on the known set of eigenvectors associated with the first section and the known characteristic matrix associated with the second section.

33. The computer-readable medium of claim 32, further comprising instructions for:
(a) obtaining a known set of eigenvalues associated with the first section;
(b) determining an auxiliary matrix based on the known set of eigenvectors and the known characteristic matrix;
(c) determining an approximated set of eigenvectors based on the auxiliary matrix;
(d) determining an approximated set of eigenvalues based on the approximated set of eigenvectors and the auxiliary matrix; and
(e) determining if a change between the known set of eigenvalues and the approximated set of eigenvalues meets a stop criterion;
(i) when the stop criterion is not met, repeating steps (b) to (e) using the determined approximated set of eigenvectors as the known set of eigenvectors in repeating step (b) and the determined auxiliary matrix as the known characteristic matrix in repeating step (b) and the determined approximated set of eigenvalues as the known set of eigenvalues in repeating step (e), and (ii) when the stop criterion is met, using the approximated set of eigenvalues as the approximated set of eigenvalues for the second section.

34. The computer-readable medium of claim 33 further comprising instructions for:
determining a set of eigenvectors for the second section based on the known set of eigenvectors associated with the first section and the one or more approximated sets of eigenvectors determined in step (c) of claim 33.

35. The computer-readable medium of claim 34, wherein the set of eigenvalues and set of eigenvalues are used in solving a system of coupled differential equations in a rigorous coupled wave analysis to generate a simulated diffraction signal for the second section.

36. The computer-readable medium of claim 35, wherein the simulated diffraction signal for the second section is stored in a library for use in a library-based process for determining the profile of a structure.

37. The computer-readable medium of claim 36, wherein the library-based process comprises:
obtaining a diffraction signal measured from directing an incident beam at the structure (a measured diffraction signal); and
comparing the measured diffraction signal to one or more simulated diffraction signals stored in the library to determine the profile of the structure.

38. The computer-readable medium of claim 35, wherein the simulated diffraction signal is generated as part of a regression-based process for determining the profile of a structure.

39. The computer-readable medium of claim 38, wherein the regression-based process comprises:
obtaining a diffraction signal measured from directing an incident beam at the structure (a measured diffraction signal);
comparing the measured diffraction signal to a first simulated diffraction signal; and
when the difference of the measured diffraction signal and the first simulated diffraction signal is not within a matching criterion:
generating a second simulated diffraction signal; and
repeating the comparing step using the second simulated diffraction signal.

* * * * *